United States Patent [19]

Ohno et al.

[11] Patent Number: 5,358,846

[45] Date of Patent: Oct. 25, 1994

[54] METHODS FOR DIAGNOSING INFECTOUS DISEASES AND METHODS FOR DETECTING AND IDENTIFYING MICROORGANISMS

[75] Inventors: Tsuneya Ohno, Tokyo; Akio Matsuhisa, Kawasaki, both of Japan

[73] Assignee: Fuso Yakuhin Kogyo Kabushiki Kaisha, Osaka, Japan

[21] Appl. No.: 449,931

[22] PCT Filed: Apr. 19, 1989

[86] PCT No.: PCT/JP89/00424

§ 371 Date: Feb. 2, 1990

§ 102(e) Date: Feb. 2, 1990

[87] PCT Pub. No.: WO89/10411

PCT Pub. Date: Nov. 2, 1989

[30] Foreign Application Priority Data

Apr. 20, 1988 [JP] Japan ............... 63-97808

[51] Int. Cl.$^5$ .............. C12Q 1/68; C12Q 1/00; C07H 17/00
[52] U.S. Cl. ................ 435/6; 435/7.1; 435/7.31; 435/7.32; 435/7.5; 435/822; 435/911; 435/973; 536/24.32; 935/76; 935/77; 935/78
[58] Field of Search .......... 435/6, 7.1, 7.31, 7.32, 435/7.5, 822, 911, 973; 536/24.32; 935/76–78

[56] References Cited

U.S. PATENT DOCUMENTS 4,689,295 8/1987 Taber et al. .................. 435/6
4,711,955 12/1987 Ward et al. .................. 536/29
4,886,741 12/1989 Schwartz ..................... 435/5

FOREIGN PATENT DOCUMENTS

WO87/05907 10/1987 PCT Int'l Appl. .

OTHER PUBLICATIONS

Sheeler and Bianchi, *Cell Biology: Structure, Biochemistry, and Function*, John Wiley & Sons, New York, 1980, p. 327.
Fall, "Analysis of Microbial Biotin Proteins", *Methods in Enzymology*, vol. 62, pp. 390–398, published 1979.
*NGN® Research Products 1988 Catalog*, supplement.
Terpstra et al., "Detection of *Leptospira interrogans* in Clinical Specimens by in situ Hybridization Using Biotin-labelled DNA Probes," *J. General Microbiology*, 133:911–914 (1987).
Takahashi et al., *Bio. Industry*, vol. 4, No. 3 (1987).
Yoshikawa, *Medical Technology*, vol. 15, No. 13 (1987).
Pardue, *In Situ Hybridisation* in Nucleic Acid Hybridisation: A Practical Approach, Chapter 8 (1985).

*Primary Examiner*—Margaret Parr
*Assistant Examiner*—Bradley L. Sisson
*Attorney, Agent, or Firm*—Marshall, O'Toole, Gerstein, Murray & Borun

[57] ABSTRACT

The invention provides methods and materials for the detection and identification of biotin-containing bacteria and/or yeast in phagocyte-containing samples obtained from patients.

8 Claims, 11 Drawing Sheets

Restriction Enzyme Maps of Probe

Probe 24 = 10.161 Kb

Probe 7 = 8.25Kb

Probe 77 = 3.052

Probe 36 = 1.967

METHODS FOR DIAGNOSING INFECTOUS DISEASES AND METHODS FOR DETECTING AND IDENTIFYING MICROORGANISMS

TECHNICAL FIELD

Field of Industrial Application

The present invention relates to systems for diagnosing infectious diseases and methods for detecting and identifying microorganisms that can be used in such systems.

BACKGROUND

Infection is the invasion and establishment of a foothold for growth in an organism by a pathogenic microorganism (hereinafter called bacterium). Whether an infection results in the outbreak of disease depends upon the interrelationship between the resistance of the host and the virulence of the bacterium.

Bacteremia may result from infection by one or more specific bacteria. Improvement in the methods of treatment of bacteremia is an important issue as shown below:

Bacteremia is not a disease caused by a specific bacterium. It is caused by the emergence and habitancy of various bacteria in blood. Its onset is clinically suspected when fever of about 40° C. persists for two or more days. Bacteremia is a serious and urgent disease, of which the primary symptom is a high fever. A patient may die within several days if not properly treated. If a patient is an infant or is suffering from terminal cancer with weakened resistance, the patient may die in one or two days.

In the case of bacteremia, phagocytes including neutrophils, ,monocytes, and macrophages primarily work in defense of the body.

Emergence of bacteria in the blood of a patient suffering from bacteremia is to the invasion of bacteria, which have avoided degradation by the phagocytes, from the tissue into the blood.

Bacteremia is a state after the above-mentioned condition has been reached. To treat bacteremia, a large amount of antibiotic to which the causative bacterium or bacteria is sensitive is administered.

Generally speaking, however, antibiotics lower the functions of the body such as the liver. Therefore, one must carefully avoid administration of an ineffective antibiotic to a patient who is seriously ill.

Bacteremia is defined as a case when the phagocytesis of cells is not able to overcome the virulence of bacteria and the bacteria spread in blood throughout the body. Sepsis is a bacteremia with serious symptoms due to toxins produced by the bacteria. Proof of sepsis (or establishment of the diagnosis) requires four important factors: 1) clinical symptoms; 2) culture; 3) gram-staining; and 4) shock state. The line of treatment is determined on the basis of these factors.

It, therefore, is essential to quickly and reliably identify the bacterium (bacteria). (The Conventional Methodology) Currently, in detection and identification of bacteria in a bacteremia-suspected specimen in a laboratory, it is a common procedure to make identification in selective media only after the specimen has been found positive in a routine process of culture bottle (hereinafter referred to as "C.B."). The rate of successful culture of bacteria from these blood specimens, however, is extremely low. Moreover, if a large dose of antibiotics is administered when bacteremia was suspected, bacteria, if any, in the blood will not be cultured and grow in many cases. The rate of C.B. positive cases, therefore, is extremely low.

Available sub-routine methods include instrumental analysis of constituents and metabolic products of bacteria (Yoshimi Benno, "Quicker identification of bacteria with gas chromatography", *Rinsho Kensa*, Vol.29, No.12, November 1985, Igaku Shoin), a method utilizing specific antibody (Japanese Patent Provisional Publication No. 60-224068), and a method based on hybridization based on specificity of DNA (Japanese Patent National Publication of the translated version No. 61-502376) which has a high accuracy due to the specificity. Separation and cultivation of a bacterium or bacteria, however, are essential pretreatment for all of these methods.

On the other hand, there is a method established based on the function of phagocytes In infectious diseases. According to that method, a stained smear of bully coat in which leukocyte of the blood sample is concentrated is examined under an optical microscope.

Generally speaking, in adult bacteremia patients, the rate of detection of bacteria in bully coat specimens is 30% at most which is identical to that in earlobe blood specimens. For newborns, however, it was reported that bacteria had been detected in 7 cases out of 10 cases (70%). The information concerning the presence of a bacterium or bacteria in peripheral blood, which is available through microscopic examination of a smear, is an important guide for treatment.

Although diagnosis of bacteremia require quick and reliability of the methods, the conventional methods hardly contribute to the treatment.

Problems to Be Solved by the Invention

In the conventional methods which necessitate pretreatment, it takes at least one or two days to selectively isolate a bacterium or bacteria from a specimen, the cultivation takes a day, and fixation one or more days. The pretreatment, therefore, requires three to four days in total. In practice, this culture is continued until the bacterium or bacteria grow, and it frequently takes more than a week even for C.B.-positive cases. This is a factor in the high mortality of C.B.-positive patients being treated by the conventional methods. For instance, according to a report published in "*The Journal of the Japanese Association for Infectious Diseases*", Vol.58, No.2, p. 122, 1984, even though the blood culture positive rate was 28.6% (163 cases/569 cases), the mortality was as high as 84.6% (138 cases/163 cases).

Moreover, it may not be possible to distinguish contamination by indigenous bacteria.

For example, *Staphylococcus epidermidis*, one of Staphylococci which are frequently found to be the causative bacteria of bacteremia, is present in the skin of a normal person. There is a risk of contamination of a specimen with this bacterium when a needle is inserted into the skin.

Furthermore, one important point is that, under the circumstances as mentioned above, many bacteria in a specimen to be cultured have been taken into said phagocyte and are dead or stationary immobilized. Consequently, the number of bacteria that can grow is small even under appropriate conditions for cultivation. As a result, the actual rate of detection of bacteria through culture of a clinical specimen is as low as about 10%.

In short, the present state is such that 90% of the examination of blood cultured for one or more days after sampling from a patient who is clinically suspected to be suffering with bacteremia do not reveal the presence of bacteria. As a result, it is the present practice, as mentioned above, to start treatment when bacteremia is clinically suspected rather than to wait for the detection result. It is a trial and error method wherein an antibiotic having broad spectrum is administered first, and if the antibiotic is not effective after one or two days, another antibiotic will be tried.

According to the staining method described in the latter part of (The Conventional Methodology), the constituents of the living body are also stained together with bacteria. It, therefore, requires experience to quickly identify bacteria according to their images; there may be cases that can be hardly diagnosed as bacteremia.

Examination of problems

Generally speaking, cells may be visualized by staining them. Cells try to digest proteins covering the exterior of invading bacteria. However, the exterior proteins will remain intact on the bacteria that have just entered. The exterior proteins, however, will be digested gradually, and then DNA and RNA will be destroyed. It, is not certain to what extent these proteins, DNA and RNA have been digested.

In any case, DNA or RNA is expected to remain in the cell for a longer period than proteins. When the objective is the identification of a bacterium or bacteria in cells, it would be more efficient and accurate to pay attention to DNA or RNA in which the degree of denaturation is low and which is well preserved rather than proteins which have been digested to a greater degree in cells. It is needless to say that this applies to a case when a bacterium itself has a resistance and remains in cells. Such bacteria include, for example, Mycobacterium, Tuberculosis, Listeria, Salmonella, Brucella, and Legionella Pneumophila, although these bacteria are not the primary causative bacteria of bacteremia. The diagnostic methods according to the present invention are applicable to these bacteria.

It has been experimentally demonstrated that the specificity of DNA or RNA of a bacterium is maintained after the bacterium has been taken into a cell.

Disclosure of the Invention

Objective of the Invention

In diagnosing an infectious disease for treatment, the ultimate objective of the examination is to confirm the presence of a bacterium or bacteria in a specimen.

The present invention is generally intended to provide the following method of (1) and the methods of (2) and (3) as steps of (1) so as to effectively execute the examination:

(1) To identify a bacterium or bacteria in a specimen which the bacterium or bacteria have been confirmed to be taken into phagocyte;
(2) To detect a bacterium or bacteria with a high rate by detecting a bacterium or bacteria which have been taken into phagocyte; and
(3) To quickly and accurately identify a bacterium or bacteria by directly detecting the bacterium or bacteria which have been taken into phagocyte without cultivation.

Summary of the Invention

[1] A system for diagnosing Infectious diseases which includes the following steps i and ii:
  i. To fix a specimen of living body constituents such as blood, ascites, or a fraction or constituent containing a large amount of phagocyte.
  ii. To identify a bacterium or bacteria in the specimen by a method including the following step ①:
    ① To hybridize the specimen by using either a radioactive probe or a non-radioactive one.

[2] A system for diagnosing infectious diseases which includes the following steps i through iii:
  i. To fix a specimen of living constituents such as blood, ascites, or a fraction or constituent containing a large amount of phagocyte.
  ii. To detect a bacterium or bacteria by a method including the following steps ① and ②:
    ① To expose the specimen to avidin-like protein such as streptavidin.
    ② To expose the above-mentioned pretreated specimen to biotin bound to a labelling molecule such as enzyme, antibody, die, or gold.
  ill. To identify a bacterium or bacteria in a specimen, in which a bacterium or bacteria have been detected in the preceding step ii, by a method including the following step ①:
    ① To hybridize the specimen by using either a radioactive probe or a non-radioactive one.

[3] A method for detecting a bacterium or bacteria in a specimen, said method including the following steps i and ii:
  i. To fix a specimen of living body constituents such as blood, ascites, or a fraction or constituent containing a large amount of phagocyte.
  ii. To identify a bacterium or bacteria in the specimen by a method including the following step ①:
    ① To hybridize the specimen by using either a radioactive probe or a non-radioactive one.

[4] A method for detecting a bacterium or bacteria in a specimen, said method including the following steps i through iii:
  i. To fix a specimen of living body constituents such as blood, ascites, or a fraction or constituent containing a large amount of phagocyte.
  ii. To expose the specimen to avidin-like protein such as streptavidin.
  iii. To expose the above-mentioned pretreated specimen to biotin bound to a labelling molecule such as enzyme, antibody, die, or gold.

[5] A method for identifying a bacterium or bacteria in a specimen, said method including the following steps i and ii:
  i. To fix a specimen of living body constituents such as blood, ascites, or a fraction or constituent containing a large amount of phagocyte.
  ii. To hybridize the specimen by using either a radioactive probe or a non-radioactive one.

Effects

The inventor found that constituents of bacterium including yeast can be quantitatively detected, irrespective of the kinds of bacteria present, by means of streptavidin or avidin bound to labelling molecules. These molecules have no affinity for phagocyte.

This is due to avidin's affinity for biotin, the binding forces of which is as high as several hundred times compared with other substances. The outer membranes of bacterial constituents are considered to be uniformly taking in biotin. Thus through the action of avidin, the presence of a bacterium or bacteria in a cell can be visualized by means of a labelling molecule with a very high sensitivity.

Furthermore, the binding speed between avidin-biotin and living body constituents is substantially greater than those of antibodies which have been used as detecting agents. Detection can be made within two to three hours with the avidin-biotin method.

For example, an enzyme used for a color reaction may be coupled, via biotin, to streptavidin which is able to bind to bacteria so that a bacterium or bacteria in a specimen can be detected by the emergence of a specific color.

The fact merits attention, that phagocytes take in and collect bacteria as mentioned above. It, therefore, is quite possible to detect DNA which are still present in bacteria which have been taken in and are being destroyed by directly treating phagocytes without cultivation and by performing in situ hybridization. As no cultivation is required, this detection method is quick and reliable.

This in situ hybridization method has been used in the field of histopathology for detecting viruses. Its application to bacterial infectious diseases has not been established yet due to the following circumstances.

Viruses grow in cell, and Free DNA or RNA that can be detected by hybridization are amply present. On the other hand, bacteria do not use such a host-dependent growth process, and the forms of bacteria which have been taken into cells are varied and complex. For Instance, preserved DNA (RNA) may be protected by bacterial constituents, or they may be in close contact with the destroyed proteins. The method, therefore, has not been tried.

The above-mentioned discussion may be summarized as follows:

(1) The characteristics of DNA or RNA of bacteria is substantially different From that of DNA or RNA of viruses, but DNA or RNA of bacteria has the highest concentration in phagocytes; and (2) The DNA (RNA) of bacteria is damaged less in phagocytes than bacterial proteins, and may be considerably well preserved in some cases.

As a result of attention given to the above-mentioned two points, the present invention has established a method for detecting bacterium or bacteria through hybridization for the first time.

If a non-radioactive probe such as a biotinylated one were used for hybridization, the detection process would be quick and simple since such a probe can be detected with an optical microscope in a conventional laboratory without radio isotope handling facilities.

The methods for diagnosing infectious diseases according to the present invention are capable of clearly and quickly detecting the presence of a bacterium or bacteria within Just two to three hours at the shortest, and one to two days at the longest, by using the two methods having the above-mentioned effects individually or in combination. In contrast, the conventional methods, such as detection by culture, require 24 or more hours to detect the presence of a bacterium or bacteria even for positive cases, and then require additional 24 to 48 hours or more to identify the bacterium or bacteria (determination of genus and species), thus a total of 3 to 4 days. The methods according to the present invention also identify the bacterium or bacteria of the detected specimen in a quick and reliable manner by using the in situ hybridization method having the above-mentioned effects. These methods, therefore, are epochal due to more accurate detection compared to the conventional methodology as a whole within one to two days at the longest. Even in cases when bacterial constituents have been mostly digested and are not detectable, the methods according to the present invention are capable of detecting their native DNA (RNA) by hybridization.

BRIEF DESCRIPTION OF THE DRAWINGS

FIG. 1: Gonococcus (particulate signal) in human cells, on Plate 1;

FIG. 2: A bacterium (not identified) taken into human leukocyte, on Plate 2 (clinical examination);

FIG. 3: Staphylococcus taken into human leukocyte, on Plate 3 (in vitro);

FIG. 4: Staphylococcus taken into murine leukocyte, on Plate 4 (in vive);

FIG. 5: Yeast from dialysate of a dialysis patient, on Plate 5;

FIG. 6: Hybrid with Staphylococcus-derived DNA taken in murine ascites, on Plate 6 (hybrid signal with Staphylococcus-derived probe);

FIG. 7: An example of the use of the method of Plate 6 with another probe, on Plate 7. No hybrid signal is present;

FIG. 8: Hybrid with DNA derived from Staphylococcus in human subphrenic abscess, on Plate 8 (hybrid signal with a probe derived from Staphylococcus);

FIG. 9: An example of the use of the method of Plate 8 with another probe, on Plate 9. No hybrid signal is present;

FIG. 10: Dot hybridization with Probe 24, on Plate 10;

FIG. 11: Dot hybridization with Probe 77, on Plate 11;

FIG. 12: Dot hybridization with Probe 7, on Plate 12;

FIG. 13: Dot hybridization with Probe 36, on Plate 13;

FIG. 14: Restriction enzyme maps of a Staphylococcus-derived probe used in an example according to the present invention;

FIG. 15: Hybrid of human blood sample and *Pseudomonas aeruginosa* derived DNA probe, on Plate 15;

FIG. 16 through FIG. 20: Hybrids between human blood samples and Staphylococcus derived DNA probe, on Plates 16 through 19, respectively.

FIG. 15, FIG. 16, FIG. 17 and FIG. 19 are optical microscope photographs with magnification of 1000 times. FIG. 18 is an optical microscope photograph with magnification of 400 times. FIG. 20 is an optical microscope photograph of the specimen of FIG. 17 with magnification of 400 times.

THE BEST FORMS OF EXECUTION OF THE INVENTION

A. Method for Preparing Specimens

Figure 1:
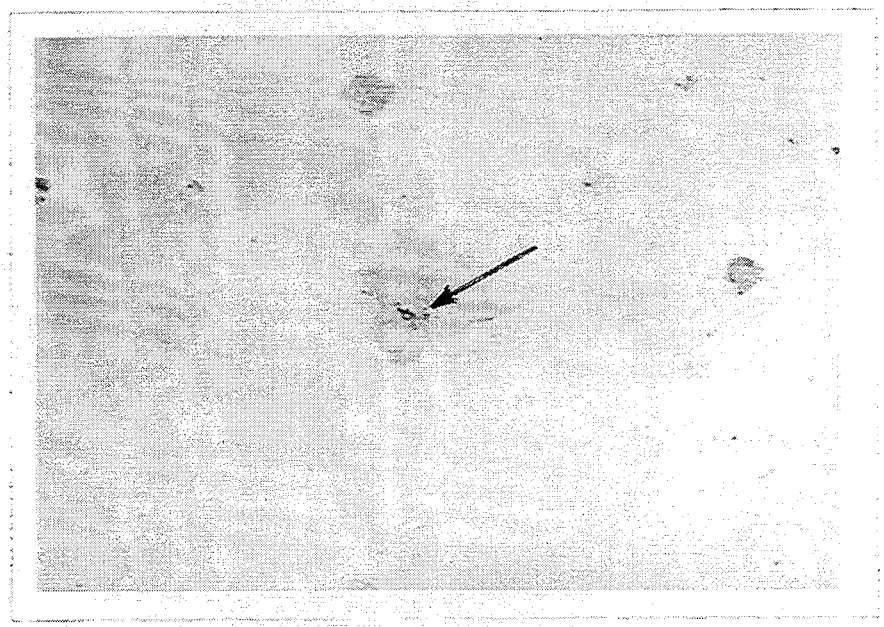
FIG. 1 through FIG. 20 represent photographs showing the forms of organisms that indicate the results of the investigation according to the present invention, and what are shown by the leader lines of the respective photographs are as follows.

Specimens prepared by the following method of (1) are fixed on slides by the method of (2) and used as samples in the respective embodiments according to the present invention:

(1) Methods for Preparing Various Clinical Specimens by Smearing

① Preparation of Samples from Blood (Heparinized Whole Bloods of Human and Animals)

Preparation of samples from blood is made by either one of the following two methods:

①-1 Mono-poly solvent (M-PRM: Flow Laboratories, Inc.) method 3 ml of M-PRM was put into a test tube of 13×100 mm, and 3.5 ml of heparinized whole blood (within two hours after sampling) being the specimen is carefully stratified over the M-PRM layer. The content of the test tube is centrifuged by a swing rotor at 300 g at room temperature for 30 minutes. Just the band of polymorphonuclear leukocyte is collected, and the band is washed with PBS (isotonic phosphate bufferred saline) and centrifuged. The resulting cell precipitate is suspended in an appropriate amount of PBS (about 1 ml) and used as specimen.

①-2 6% dextran method

One volume (1 ml) of heparinized whole blood being a specimen is mixed with ⅛-¼ volume of 6% dextran, and the mixture is left to stand at 37° C. for one hour. The upper layer is collected and diluted with PBS, and subjected to centrifugation. The resulting cell precipitates are suspended in an appropriate amount of PBS and used as specimen.

② Preparation of Samples from Urine

Urine specimen is directly smeared.

③ Preparation of Samples from Ascites

Ascites is transferred to a test tube, and centrifuged at 800 r.p.m. or 3,000 r.p.m. at room temperature for 15 to 30 minutes. The resulting cell precipitates are suspended in an appropriate amount of PBS and used as specimen.

④ Preparation of Samples from Pus

Pus specimen is directly smeared.

(2) Method for Smearing and Fixing Sample on Microscope Slide

An appropriate amount of a specimen obtained by the operation of (1) is placed on a 2% gelatin-coated slide (preferably "H. T. Coating Slide", Boxy Brown) and extended by the side of a pipette, and completely air-dried. Next, the slide is immersed in Carnoy's B fixative (ethanol:chloroform:acetic acid=6:3:1) for 10 minutes to fix the cells. Then the slide is lightly washed in ethanol and air-dried.

Experimental Part 1 Method for Detecting Bacterium or Bacteria by Means of Avidin-like Protein (hereinafter referred to as the streptavidin method)

Streptavidin is used as an avidin-like protein in the present experiment.

Each sample fixed on a slide prepared by the abovementioned method A is rehydrated in PBS at room temperature for 10 minutes or over, and an appropriate amount of PBS containing 5 μg/ml of streptavidin (Amersham), 1% bovine serum albumin (Sigma Fraction V) and 0.1% Tween 20 (polyoxyethylene sorbitan monolaurate)(Sigma) is placed on the fixed sample and allowed to react at 37° C. in a moisture chamber for 60 minutes. The fixed sample is then lightly shaken in an appropriate amount of PBS containing 0.1% Tween 20 (polyoxyethylene sorbitan monolaurate) to be washed at room temperature for 10 minutes for three times.

Next, a PBS containing 5 μg/ml of biotinylated alkaline phosphatase (E. Y LABS. Inc.), 1% bovine serum albumin and 0.1% Tween 20 (polyoxyethylene sorbitan monolaurate) is placed on the fixed sample on slide, and is allowed to react at 37° C. in a moisture chamber for 60 minutes. Then the fixed sample is lightly shaken in a PBS containing 0.1% Tween 20 (polyoxyethylene sorbitan monolaurate) and washed at room temperature for 10 minutes once. Furthermore, the fixed sample is lightly shaken in AP7.5 (100 mM Tris-HCl pH 7.5, 100 mM NACl) containing 0.05% Triton (octyl phenoxyl polyethoxyethanol) (Sigma) (hereinafter referred to as TX) and washed at room temperature for 10 minutes twice. Then the fixed sample is lightly shaken in AP9.5 (100 mM Tris-HCl pH9.5, 100 mM NACl, 10 mM MgCl) and washed at room temperature for 10 minutes three times.

The fixed sample is then placed in AP9.5 containing 0.3 mg/ml of NBT (nitroblue tetrazolium, Bethesda Research Laboratories) and 0.17 mg/ml of BCIP (5-bromo-4-chloro-3-indolyl phosphate, Bethesda Research Laboratories) at 37° C. in the dark to make color reaction. The reaction is terminated by immersing the sample in 10 mM EDTA for several minutes. The sample is then air-dried.

Finally, contrast staining of the sample is made with Naphthol Blue Black (Sigma) of an appropriate concentration. The sample is washed in running water, and completely air-dried. The sample is then oil-immersed and observed under a microscope to check for the presence of a bacterium or bacteria (signal).

Bacteria are observed as purple signals and cells such as neutrophil as water-color or blue signals.

In the following, the results of the exemplary experiments on the respective plates will be explained with reference to the leader lines drawn on the microphotographs of the plates.

An optical microscope with magnification of 1000 times was used.

Plate 1

A bacterium (Gonococcus) in urine (clinical specimen);

Gonococcus in human cells were observed as particulate signals stained in blue. (FIG. 1)

Plate 2

A bacterium (not identified) detected in human blood (clinical specimen);

The blood preparation method was the dextran method.

Figure 2:
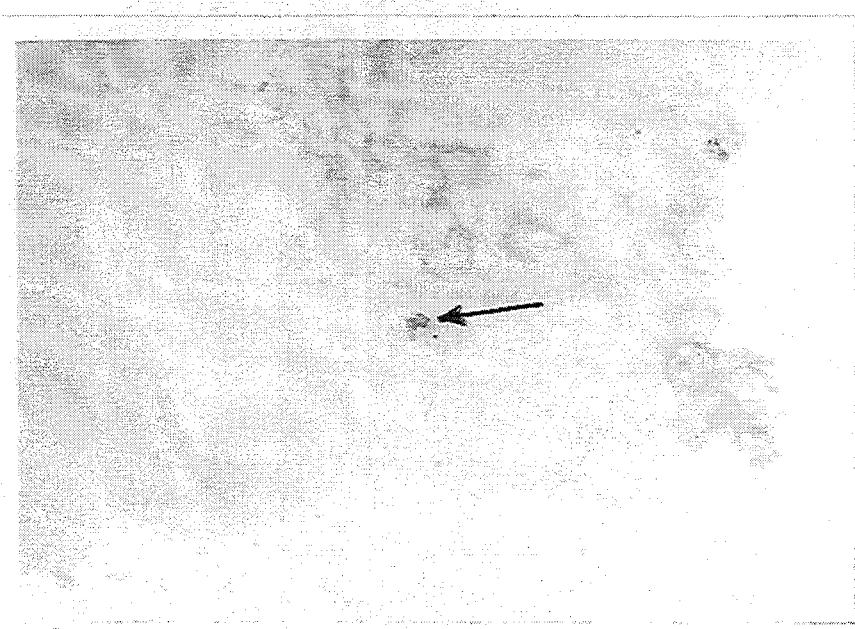

The bacterium taken in human leukocyte was observed. (FIG. 2)

Plate 3

Staphylococcus detected in human blood (in vitro);

The blood preparation method was the mono-poly solvent method. Blood and Staphylococcus were Incubated for 20 minutes.

Figure 3:
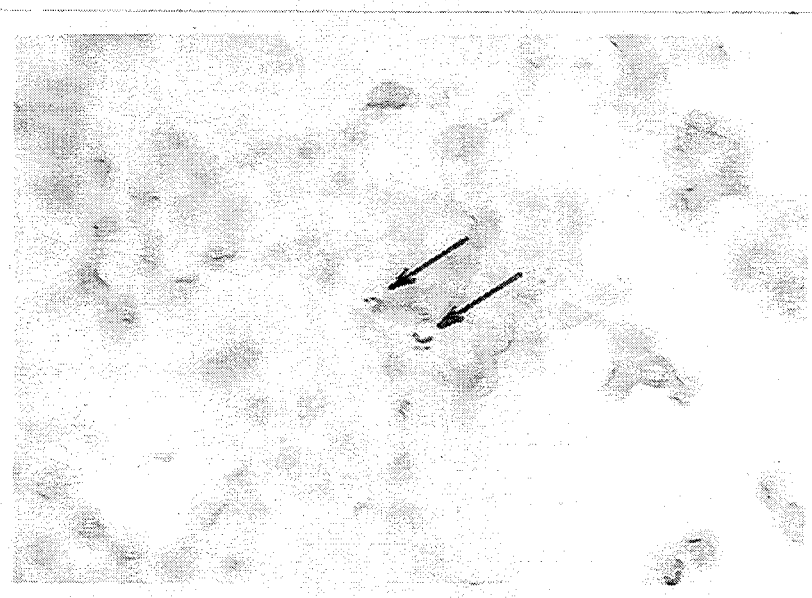

Signals indicating Staphylococcus taken in human leukocyte were observed. (FIG. 3)

Plate 4

Staphylococcus detected in human blood (in vivo);

Staphylococcus was injected into a mouse intravenously, and after 4 hours, blood was sampled according to the conventional method.

Figure 4:
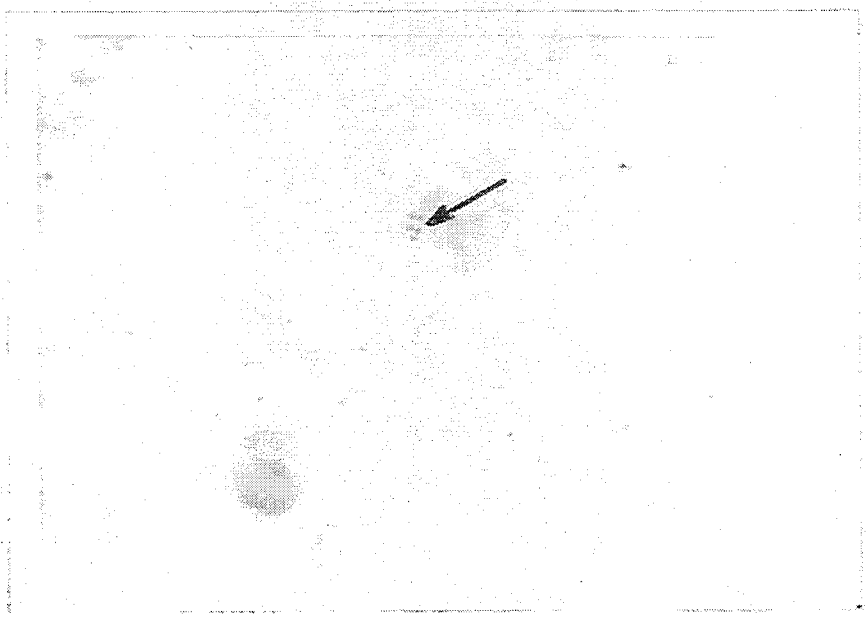

Signals indicating Staphylococcus taken in murine leukocyte were observed. (FIG. 4)

Plate 5

Yeast detected in dialysate after peritoneal dialysis;

The specimen was obtained from a dialysis patient.

Figure 5:

Signals indicating yeast from the dialysate of the dialysis patient were observed. (FIG. 5)

The preparation method of Plates 2, 3 and 4 may be either the dextran method or the mono-poly solvent method.

Experimental Part 2 Detection and Identification of Bacterium or Bacteria (Infectious Bacterium or Bacteria) in or out of Cells through In situ Hybridization with Biotinylated Probe (hereinafter referred to as the probe method)

Each sample fixed on a slide prepared by the above-mentioned method A is immersed in PBS at room temperature for 10 minutes or over to rehydrate it, and then immersed in a PBS containing saponin and TX by 0.25% (w/v), respectively, and lightly shaken at room temperature to treat it for 10 minutes.

Next, about 100 ml of PBS-saponin (0.05% solution containing 5 mg/ml each of lysozyme (Sigma) and of Lysostaphin (trade name, Sigma) and 0.5 mg/ml of N-acetylmuramidase SG (trade name, Seikagaku-Kogyo) is added to each well. The sample is allowed to stand at room temperature or at 37° C. in a moisture chamber for 120 minutes. Then the sample is washed with physiological saline containing 0.2N HCl for 20 minutes. Next, the sample is immersed in 0.1M triethanolamine-HCl buffer (pH 8.0) containing 0.5% acetic anhydride for 20 minutes.

After that, each slide is washed with 75% ethanol, and then with 95% ethanol, and sufficiently air-dried. Next, the slide is immersed in physiological saline solution containing 70 mM NaOH for three minutes, and immediately washed with 70% ethanol and then with 95% ethanol, and then sufficiently air-dried and used as a sample for in situ hybridization.

Next, an appropriate amount of a hybridization solution of the following composition is placed on the sample fixed on the slide, and the sample is allowed to react at 37° C. in a moisture chamber for one day.

Composition

45% formamide
2×SSC
1×Denhardt's solution [0.02% polyvinylpyrrolidone (Sigma), 0.02% Ficoll® (synthesized macromolecular substance prepared from sucrose (Pharmacia Fine Chemicals), 0.02% bovine serum albumin]
250 μg/ml of salmon sperm DNA [denatured beforehand by heating it at 100° C. for five minutes and chilled in ice (Pharmacia Fine Chemicals)]
10% Dextran Sulfate (Pharmacia Fine Chemicals)
An appropriate amount of biotinylated probe DNA (denatured beforehand). Biotinylation of the probe DNA is prepared by nick translation. For example, a nick translation kit (Bethesda Research Laboratories) is used.

Next, the sample is washed in 2×SSC containing 50% formamide at 37° C. for 30 minutes, then in 1×SSC containing 50% formamide at 37° C. or over for 30 minutes. Furthermore, the sample is lightly shaken in 1×SSC and washed at room temperature for 20 minutes three times. Then the sample is immersed in PBS at room temperature for 10 minutes.

In succession, to effect blocking, PBS containing 10% normal rabbit serum (Vector Laboratories Inc.) is placed on the sample fixed on slide, and the sample is then incubated at 37° C. in a moisture chamber for 60 minutes, and immersed in PBS at room temperature for several minutes.

Next, PBS containing 2 μml of streptavidin, 1% bovine serum albumin, and 0.1% Tween 20 is placed on the sample fixed on slide, and the sample is incubated at 37° C. in a moisture chamber for 60 minutes, and then lightly shaken and washed in PBS containing 0.1% Tween 20 (polyoxyethylene sorbitan monolaurate) at room temperature for 10 minutes three times.

Next, PBS containing 2 μg/ml of biotinylated alkaline phosphatase, 1% BSA, 0.1% (polyoxyethylene sorbitan monolaurate) is placed on the sample fixed on slide, and the sample is incubated at 37° C. in a moisture chamber for 60 minutes. Then the sample is lightly shaken and washed in PBS containing 0.1% (polyoxyethylene sorbitan monolaurate) at room temperature for 10 minutes. The sample is then lightly shaken and washed in AP7.5 containing 0.05% TX at room temperature for 10 minutes twice. Then the sample is lightly shaken and washed in AP9.5 at room temperature for 10 minutes three times.

Next, the sample is immersed in AP9.5 containing 330 μg/ml of NBT and 170 μg/ml of BCIP at 37° C. in the dark for an appropriate time to allow the color reaction to take place The reaction is terminated by immersing the sample in 10 mM EDTA for several minutes, and the sample is air-dried.

Finally, contrast staining of the sample is made with Naphthol Blue Black of an appropriate concentration The sample is washed in running water, and completely air-dried. The sample is then oil-immersed and observed under a microscope to check for the presence of a bacterium or bacteria on the basis of color reaction and unique form.

In the following, the results of the experiments will be illustrated with reference to the leader lines drawn on the microphotographs of the plates. An optical microscope with magnification of 1000 times was used.

Experiment 1 Preparation of staphylococcus-derived DNA Probe

The properties of the Staphylococcus-derived DNA probe used in the following Exemplary Experiments 2 and 3 were as follows:

The preparation method used the cloning technology established in a text, for example, "Guide to Molecular Cloning Techniques", Methods in ENZYMOLOGY, vol., 152, Academic Press 1987, and Staphylococcus chromosomal DNA was inserted into a vector (e.g. pBR).

Clones having DNA fragments unique to Staphylococcus were selected from the resulting clones, and they were used as probes.

These probes do not cross hybridize with other bacteria (such as *Escherichia coli*, Klebsiella, Pseudomonas, Enterobacter, and *Staphylococcus epidermidis* of the same genus).

Figure 14:
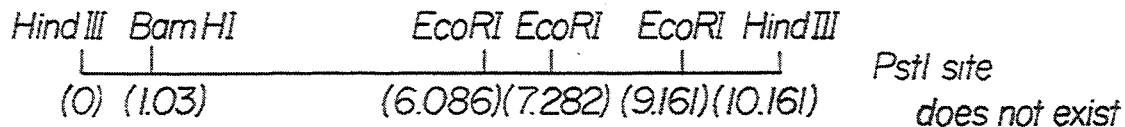
Figure 14:
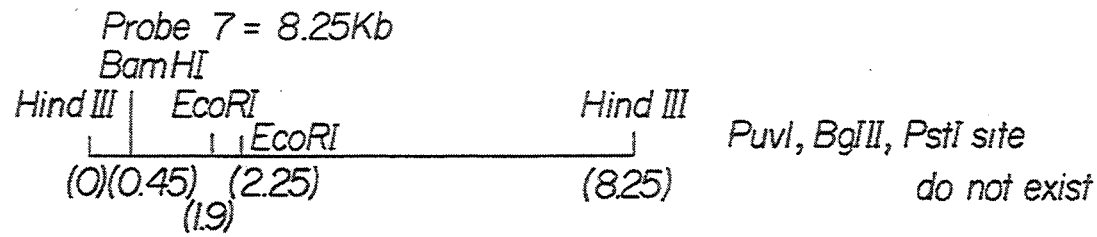
Figure 14:
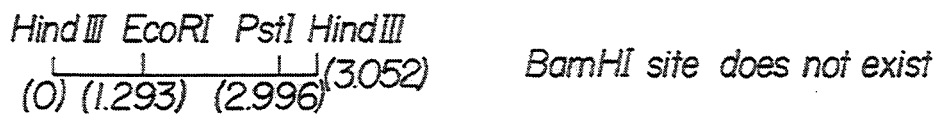
Figure 14:

The restriction map of these probes is as shown in FIG. 14.

The reactivity between these probes and clinical strains (*Staphylococcus aureus* and *Staphylococcus epiderimidis*; a priority was given to these species since they are the most frequently causative bacteria of infectious diseases and they are the same species) was examined as follows:

Preparation Method

The preparation method was based on the above-mentioned text, and clinical bacterial strains were cultured and their DNA were extracted.

A certain amount (e.g. 5 μl) of each extract was spotted on a nylon filter and subjected to alkaline denaturation. After that, they were used as samples of hybridization.

Dot Blot Hybridization

According to said text, hybridization was made with the above-mentioned =P -labelled probes in 50% formamide 5×SSC at 42° C. all night.

After that, samples were washed with 0.1×SSC, 0.1% SDS, at 55° C. for 20 minutes twice, then subjected to irradiation at −70° C. all night. Then the samples were developed.

The reactivities between these probes and clinical strains (Staphylococcus aureus and Staphylococcus epidermidis) are shown by Plates 10, 11, 12 and 13.

In each case, signals are observable in places where Staphylococcus aureus was spotted (spots of the upper two rows of FIGS. 10, 11, 12, and 13), and no signals are observable in places where Staphylococcus epidermidis was spotted (spots of the lower two rows of said figures). Hence these probes reliably detect Staphylococcus aureus but do not cross with Staphylococcus epidermidis which is the same species as Staphylococcus aureus.

Exemplary Experiment 2 Detection of Staphylococcus in Murine Ascites

Staphylococcus was injected into the abdominal cavity of a mouse, and laparotomy was made 4–6 hours after the injection to collect ascites. The ascites was treated according to the above-mentioned preparation method A (1) ③, and the resulting centrifuge precipitate was suspended in 100 μl of PBS, and 20–50 μl of the suspension was placed in a well of each object glass to prepare a fixation sample. According to the method described in the above-mentioned Exemplary Embodiment 1, the following probes were used to hybridize the sample.

The results of the experiment are shown by each experimental plate.

Figure 6:
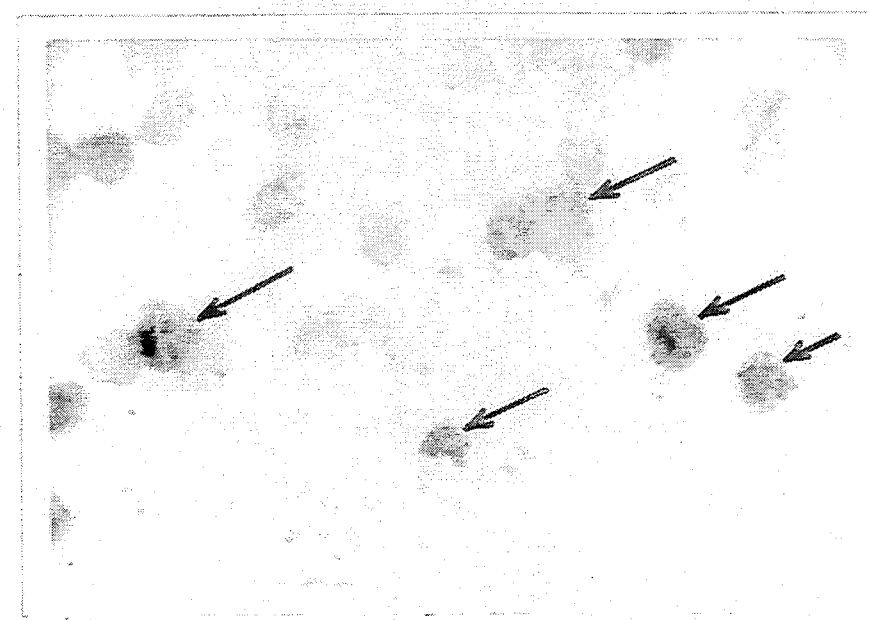

Plate 6
Hybridization between Staphylococcus taken in ascites and Staphylococcus-derived DNA probe;
Signals indicating hybrid were observed. The signals indicated dispersion of leukocyte. (FIG. 6)

Figure 7:
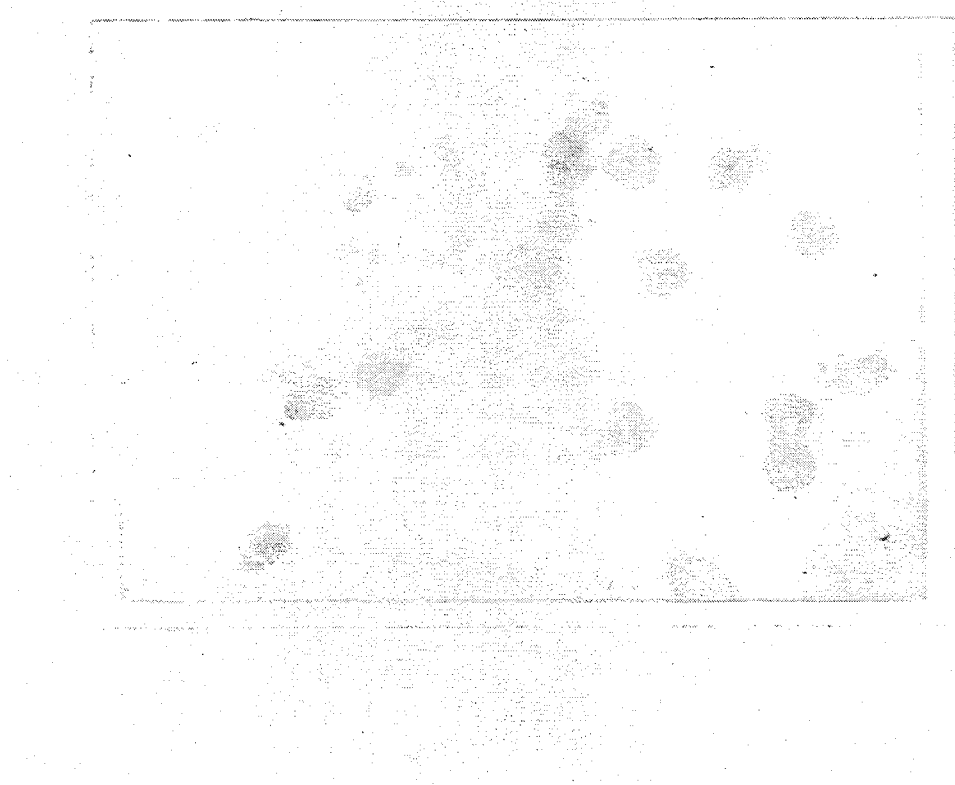

Plate 7
Hybridization using Esherichia coli-derived and Klebsiella-derived probes;
No signal of hybridization was detected. (FIG. 7)

Exemplary Experiment 3 Detection of Staphylococcus in Human Subphrenic Abscess A specimen of human subphrenic abscess was suspended in physiological saline, and 20 μl of the suspension was smeared and spread in each well and then air-dried (for 40 minutes). After that, the samples were pretreated in the same manner as Plates 6 and 7, and then subjected to in situ hybridization by the method of Experimental Part 1.

The results of the experiment are shown below by experimental plate.

Figure 8:
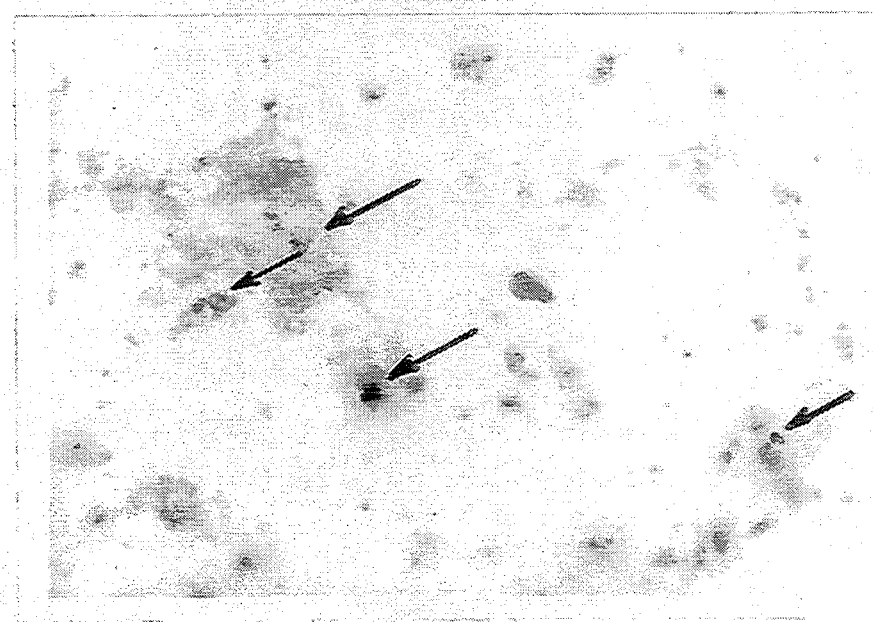
Figure 9:
Figure 10:
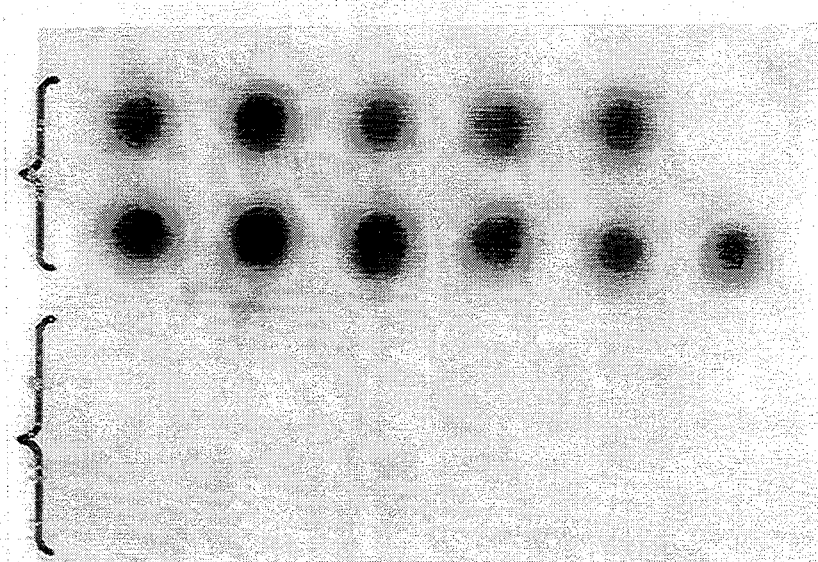
Figure 11:
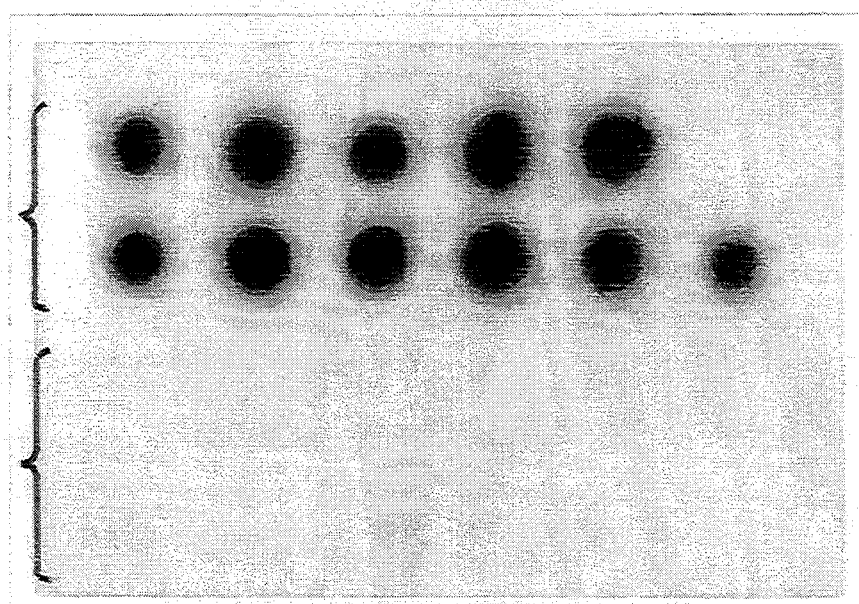
Figure 12:
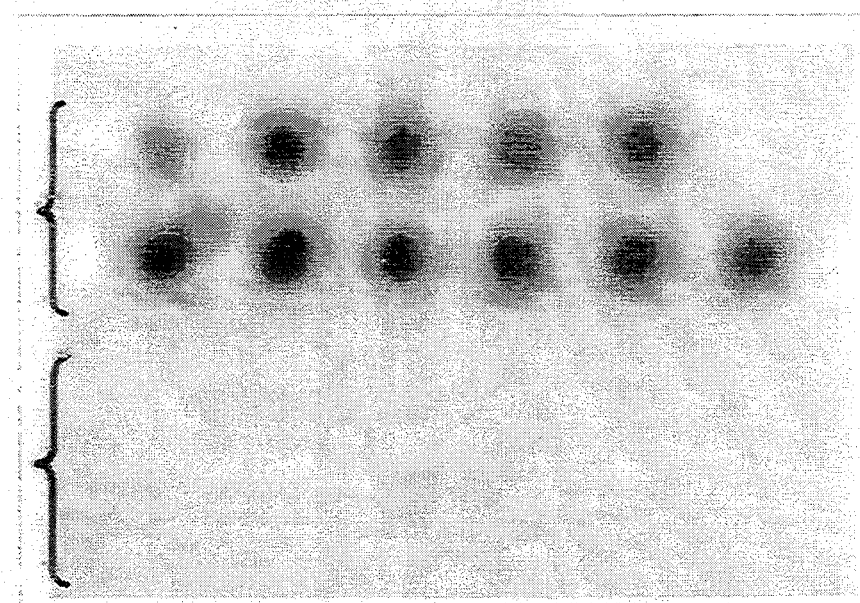
Figure 13:
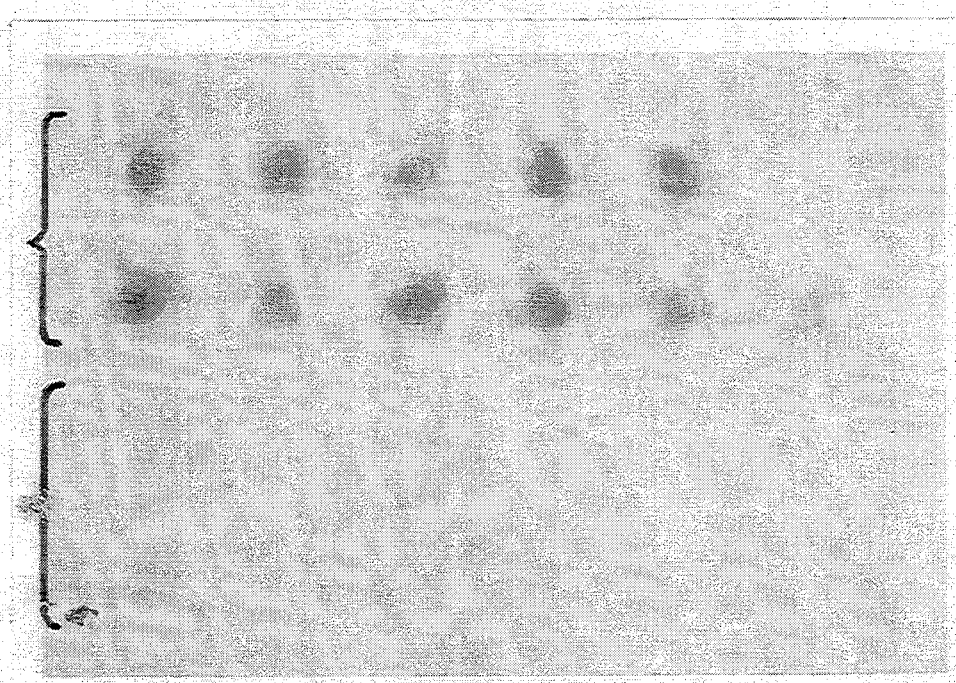

Plate 8
Hybridization with the DNA probe used for Plates 6 and 7;
Signals of hybrid were observed. (FIG. 8)

Plate 9
Hybridization with the same probe used for Plates 6 and 7;
When Escherichia coli-derived and Klebsiella-derived DNA probes were used, no signal of hybrid was detected.

Experimental Part 3 Comparative Experiment of In Situ Hybridization Method and Blood Culture Method From a patient in whom no bacterium was detected by the streptavidin method of the above-mentioned Experimental Part 1, human blood samples were prepared by using the 6% dextran method of said A (1)①-2 and the method for smearing and fixing sample on slide of said A (2). According to the method described in Experimental Part 1, the samples were hybridized with the Staphylococcus-derived DNA probe prepared in Exemplary Experiment 1 (see Plates 16 through 19 of Table I below, and FIGS. 16 through 19).

Pseudomonas aeruginosa-derived DNA probe was also prepared by a method similar to the method for preparing the DNA probe of Exemplary Experiment 1. To be more specific, chromosome DNA of Pseudomonas aeruginosa was fragmented by restriction enzyme Hind III and insert into an appropriate vector (e.g. pBR322) to amplify the fragments. Those which do not cross with other bacterial DNAs (such as Escherichia coli, Klebsiella, Enterobacter, and Staphylococcus) were selected. Then those having appropriate length (for example, 10 kb, 5 kb, 4.5 kb) were selected as probes.

Figure 15:
Figure 16:
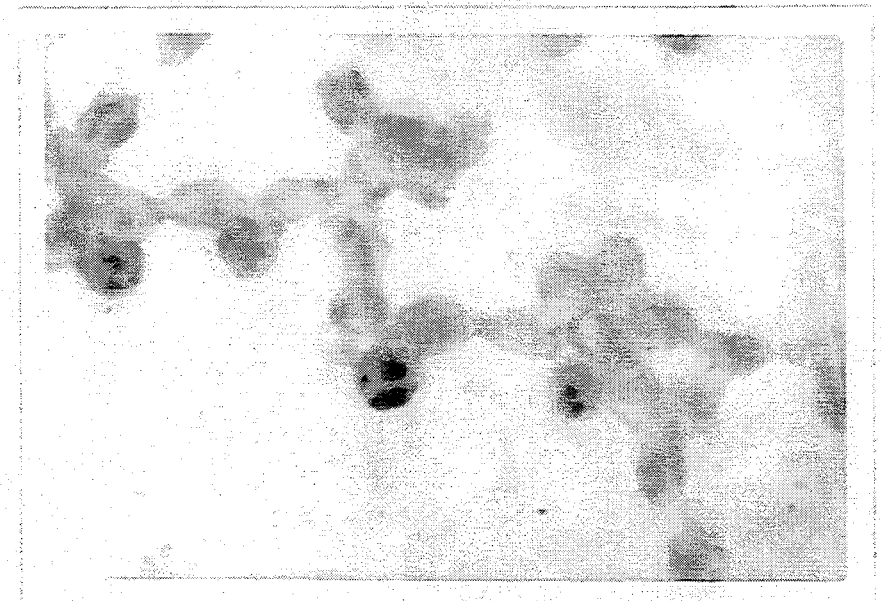
Figure 17:
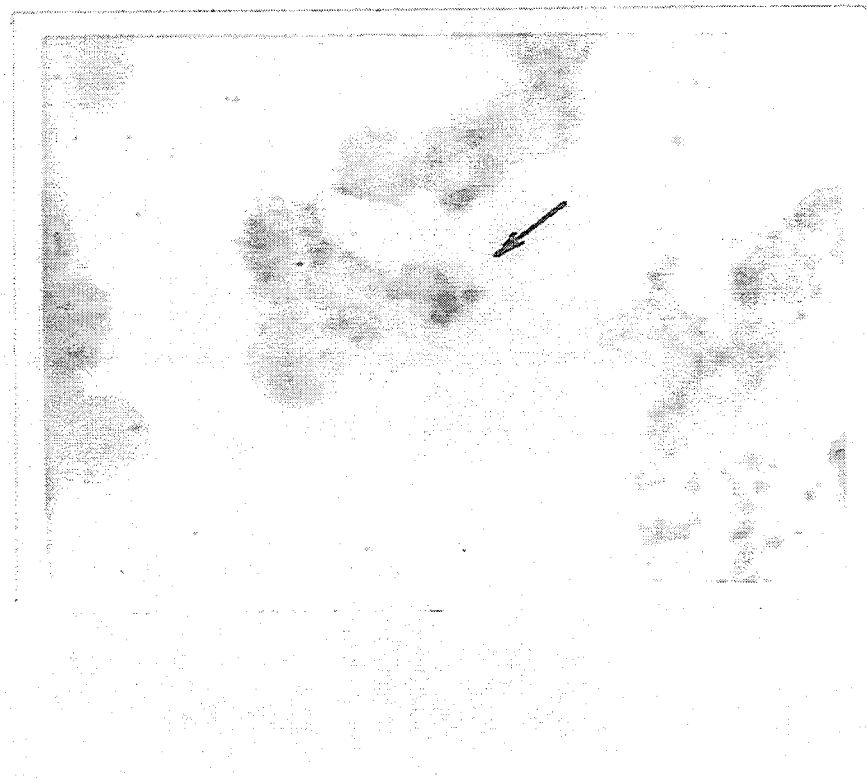
Figure 18:
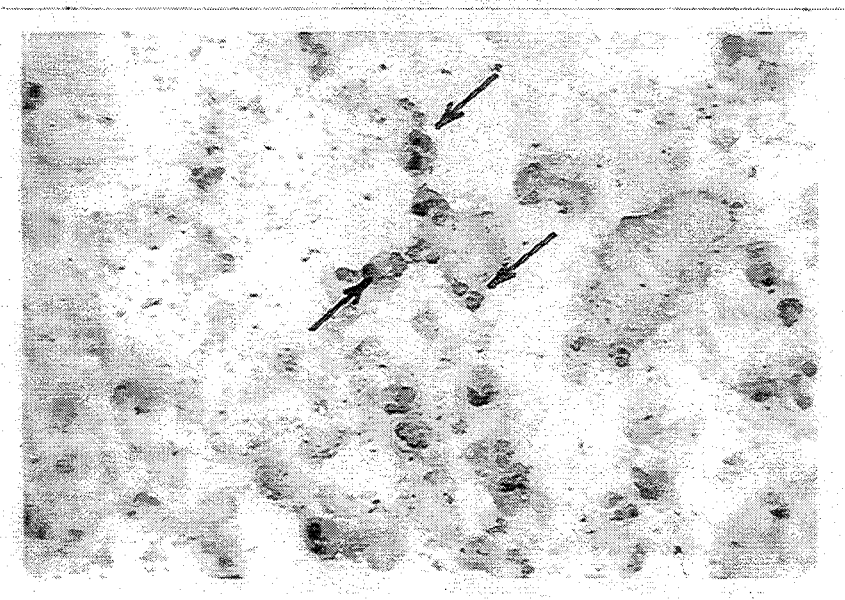
Figure 19:
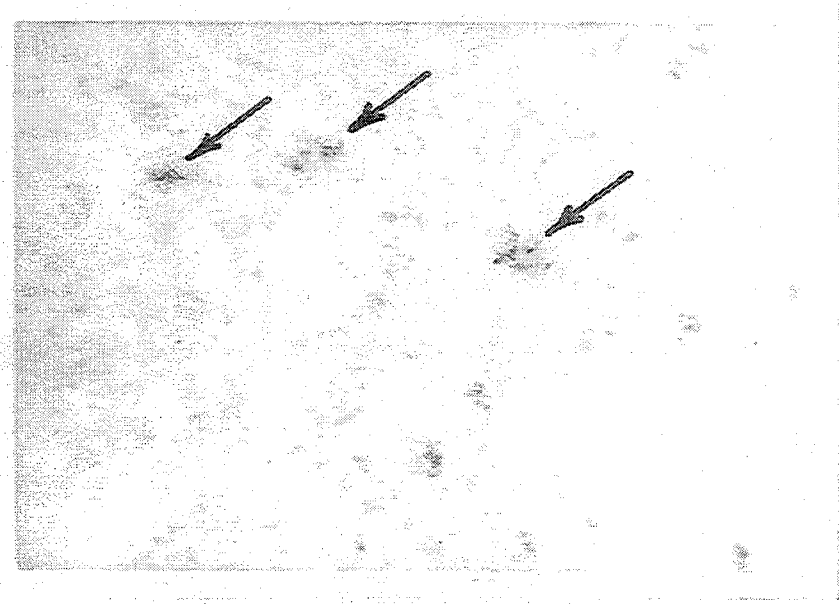
Figure 20:
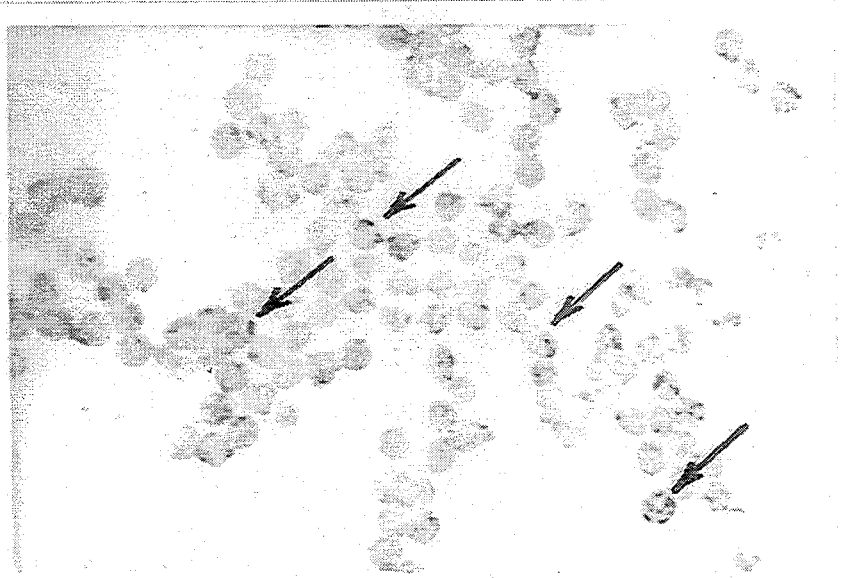

In accordance with the method described in said Experimental Part 1, one of the probes was hybridized with the human blood samples prepared as described above (see Plate 15 of Table I below, and FIG. 15).

Using a blood collecting unit "Roche", blood was aseptically collected from the vein of the same patient from whom the above-mentioned human blood samples were taken. Blood was collected In Liquoid BC bottle "Roche" (Nippon Roche KK), 10 ml each. The specimens were incubated at room temperature, and the specimens were monitored day by day. As a result, as shown in Table I below, no bacterium was detected in Bottles 15 through 19 (no microphotographs are indicated).

The above-mentioned results are summarized in Table I below.

TABLE I

Results of Comparative Experiment of the Probe Method and the Blood Culture Method

| Plate or Bottle No. | Name of bacterium detected by the probe method | Blood culture method, in 1 month |
|---|---|---|
| 15 | Pseudomonas aeruginosa | —* |
| 16 | Staphylococcus aureus | — |
| 17 | " | — |
| 18 | " | —** |
| 19 | " | — |

Notes:
*Pseudomonas aeruginosa was detected from sputum.
**Staphylococcus aureus was detected from feces.

As clearly shown by the results of Table I above, it was demonstrated that the use of the probe method allowed detection of a bacterium from specimens from which no bacterium had been detected by the conventional blood culture method and the direct streptavidin method, and that the detection capability of the probe method was excellent.

Effects of the Invention

First, the in situ hybridization method, which was directed to phagocyte, was capable of quickly and reliably identifying a bacterium in a specimen which was not positive according to the blood culture. Hence the establishment of this diagnostic method will give a epochal guidance to the treatment of bacteremia, and reduction in mortality is expected.

According to the conventional blood culture method, it was necessary, in preparation of specimen, to take about 5 to 10 ml of blood sample from a patient day after day until the bacterium is detected, and the patient had to suffer physically as well as mentally. In contrast with conventional methods, it is sufficient, under the presently-claimed method, to take a blood sample from a patient only once, and no exact sterile operation is needed. Furthermore, a very small sample quantity will do. For instance, the dextran method requires only about 1 ml. Thus physical and mental suffering of the patient can be reduced.

According to the method for diagnosing infectious diseases of the present invention, which uses the probe method alone, it is possible to detect and identify bacterium or bacteria in a specimen from which no bacterium was detected by the streptavidin method, and the detection and identification capabilities are markedly great.

Furthermore, the detection method of the present invention, which uses the streptavidin method alone, quickly gives a very clear detection result. This invention marks progress in the set in the sense that it allows confirmation of bacteremia in circumstances for which the conventional approach had to tentatively start treatment with antibiotics on the basis of clinically suspected bacteremia.

The detection and identification methods of the present invention, which use the probe method alone, have the following effects with regard to the identification of causative bacterium or bacteria of bacteremia. According to the present hybridization method, one specimen allows identification of the type of bacterium, the time required can be significantly reduced, and the detection rate is markedly high. The conventional method took three or four days to accomplish the same result (and the detection rate was low).

When non-radioactive labels, in particular, biotinylated probes are used, the present method can be used easily irrespective of the tissue type.

However, with regard to the presently-claimed DNA hydribization method, further research is needed to find probes with specificity is as high as possible.

For example, if a DNA probe which is specific to *Staphylococcus aureus* only was developed and used, the detection result will be negative for a specimen in which no *Staphylococcus aureus* is present. If the specimen was checked by changing time kinds of probe one after another and found to be negative for all DNA, the presence of a bacterium will be uncertain.

Of the methods for diagnosing infectious diseases according to the present invention, the diagnostic method using the streptavidin method and the probe method in combination quickly detects a specimen in which a bacterium is present and then quickly and reliably identifies time bacterium of the specimen. The whole process of the method, therefore, is quick and reliable.

The confirmation of time presence or absence of bacterium by means of the streptavidin method is quite useful in preventing costly repetition of hybridization of specimens having no bacterium.

Furthermore, in contrast with the conventional staining method, the present method does not stain the living body constituents. It specifically stains bacterium or time like in the specimen. It, therefore, allows quick and reliable judgement of the infection state, and no special skill is required.

We claim:

1. In a method for detecting biotin-containing bacteria or yeast in a sample obtained from a patient comprising fixing a phagocyte containing specimen obtained from the patient on a solid support for a time and under conditions sufficient for said phagocytes to become fixed to said support, the improvement comprising exposing the fixed phagocytes to a reagent having a preferential binding affinity for biotin, and detecting any product formed by binding of the reagent to bacterial or yeast biotin contained within said fixed phagocytes.

2. The method of claim 1 wherein said reagent is selected from the group consisting of avidin or streptavidin.

3. The method of claim 1 wherein the step of detecting said product comprises exposing said product to biotin labelled with a detectable label and detecting any complex formed between the product and the labelled biotin.

4. The method of claim 1 wherein said detectable label is an enzyme, an antibody, a dye, gold, or a radioisotopic element.

5. The method of claim 1 wherein the phagocyte-containing specimen is selected from the group consisting of blood, ascites fluid and pus.

6. The method of claim 1 wherein said specimen is fixed to said solid support by a fixing step which comprises immersing the specimen in Carnoy's B fixative.

7. The method of claim 1 further comprising identification of the specific bacteria or yeast causative agent of an infection detected by means of the formation of said product through the subsequent step of hybridization of bacteria or yeast nucleic acids in said fixed phagocytes with one or more detectable oligonucleotide probes specific for bacterial or yeast species.

8. The method of claim 7 wherein said detectable oligonucleotide probe or probes are labelled with an enzyme, an antibody, gold, or a radioisotopic element.

* * * * *

UNITED STATES PATENT AND TRADEMARK OFFICE
CERTIFICATE OF CORRECTION

PATENT NO. : 5,358,846
DATED : October 25, 1994
INVENTOR(S) : T. Ohno and A. Matsuhisa It is certified that error appears in the above-indentified patent and that said Letters Patent is hereby corrected as shown below:

Column 1, Line 35, second comma should be deleted.

Column 2, line 19, "In" should be lowercase.

Column 2, line 21, "bully" should be "buffy"

Column 2, line 24, "bully" should be "buffy"

Column 4, line 1, "Infectious" should be lowercase.

Signed and Sealed this

Eighth Day of August, 1995

Attest:

BRUCE LEHMAN

Attesting Officer

Commissioner of Patents and Trademarks